US009822167B2

(12) United States Patent
Benyacoub et al.

(10) Patent No.: US 9,822,167 B2
(45) Date of Patent: *Nov. 21, 2017

(54) PROBIOTICS, SECRETORY IGA AND INFLAMMATION

(75) Inventors: Jalil Benyacoub, Lausanne (CH);
Blaise Corthesy, Lausanne (CH);
Stephanie Blum-Sperisen, Pully (CH);
Laurent Favre, Puidox-gare (CH)

(73) Assignee: Nestec S.A., Vevey (CH)

( * ) Notice: Subject to any disclaimer, the term of this patent is extended or adjusted under 35 U.S.C. 154(b) by 693 days.

This patent is subject to a terminal disclaimer.

(21) Appl. No.: 13/000,666

(22) PCT Filed: Jun. 16, 2009

(86) PCT No.: PCT/EP2009/057453
§ 371 (c)(1),
(2), (4) Date: Feb. 25, 2011

(87) PCT Pub. No.: WO2009/156301
PCT Pub. Date: Dec. 30, 2009

(65) Prior Publication Data
US 2011/0268743 A1 Nov. 3, 2011

(30) Foreign Application Priority Data
Jun. 24, 2008 (EP) .................... 08158827

(51) Int. Cl.
*A61K 39/00* (2006.01)
*A61K 39/40* (2006.01)
*A61K 39/395* (2006.01)
*C12N 5/07* (2010.01)
*A61K 39/385* (2006.01)
*A61K 39/02* (2006.01)
*C07K 16/12* (2006.01)
*A61K 35/744* (2015.01)
*A61K 35/745* (2015.01)
*A61K 35/747* (2015.01)

(52) U.S. Cl.
CPC ........ *C07K 16/1228* (2013.01); *A61K 35/744* (2013.01); *A61K 35/745* (2013.01); *A61K 35/747* (2013.01); *A61K 2039/505* (2013.01); *A61K 2039/6037* (2013.01); *A61K 2123/00* (2013.01)

(58) Field of Classification Search
CPC .. A61K 2300/00; A61K 35/74; A61K 35/745; A61K 35/744; A61K 35/741; A61K 35/747; A61K 38/00; A61K 39/395; A61K 39/0208; A61K 39/09; A61K 2039/542; A61K 2039/505; A23V 2002/00; A23V 2200/3204; A23V 2200/324; A23V 22/3202; A23V 2200/32; A23L 1/3014; A23L 1/296; A23L 1/0345
See application file for complete search history.

(56) References Cited

U.S. PATENT DOCUMENTS

| 5,531,988 | A | * | 7/1996 | Paul | 424/93.4 |
| 2005/0079244 | A1 | * | 4/2005 | Giffard et al. | 426/42 |
| 2008/0145420 | A1 | * | 6/2008 | Simon | 424/463 |
| 2011/0130545 | A1 | * | 6/2011 | Hensgens et al. | 530/387.1 |
| 2012/0014963 | A1 | * | 1/2012 | Benyacoub et al. | 424/157.1 |

FOREIGN PATENT DOCUMENTS

| EP | 1661983 | | 5/2006 |
| EP | 2127661 | A1 * | 2/2009 |
| EP | 1854467 | | 5/2011 |
| JP | S5589233 | | 7/1980 |
| JP | H4342533 | | 11/1992 |
| JP | H06234647 | | 8/1994 |
| JP | H0761934 | | 3/1995 |
| WO | 9720577 | | 6/1997 |
| WO | WO 2007/019901 | | 2/2007 |
| WO | WO 2008/064489 | | 6/2008 |
| WO | 2009156301 | | 12/2009 |

OTHER PUBLICATIONS

Yuvaraj et al., Mol. Nutr. Food Res., 2008 (article 1st published online May 26, 2008); 52: 913-920.*
Pant et al., BMC Microbiology, Sep. 2007; 7(86): 1-9.*
Fedorak et al., Current Opinion in Gastroenterology, 2004, 20: 146-155.*
http://www.mayoclinic.com/health/pseudomembranous-colitis/DS00797, accessed on Dec. 25, 2013.*
Mantis et al., Mucosal Immunology, 2011; 4(6): 603-611.*
Pant, N., et al., "Effective prophylaxis against rotavirus diarrhea using a combination of Lactobacillus rhamnosus GG and antibodies," BMC Microbiology, vol. 7, No. 86, Sep. 27, 2007, pp. 1-9, XP 021013260.
Phalipon, A., et al., "Novel functions for mucosal SIgA," Mucosal Immune Defense: Immunoglobulin A Springer, 2007, pp. 183-202, XP009107522.
Corthesy, B., et al., "Recombinant secretory immunoglobulin A in passive immunotherapy: Linking immunology and biotechnology," Current Pharmaceutical Biotechnology, vol. 4, No. 1, Feb. 1, 2003, pp. 51-67, XP009094155.
Corthesy, B., et al., "Secretory immunoglobulin A: From mucosal protection to vaccine development," Biological Chemistry, vol. 380, No. 11, Nov. 1999, pp. 1251-1262, XP009107514.
Pant, N., et al., "Lactobacilli expressing variable domain of llama heavy-chain antibody fragments (lactobodies) confer protection against rotavirus-induced diarrhea," Journal of Infectious Diseases, vol. 194, No. 11, Dec. 1, 2006, pp. 1580-1588, XP009107245.

(Continued)

*Primary Examiner* — Gary Nickol
*Assistant Examiner* — Lakia Jackson-Tongue
(74) *Attorney, Agent, or Firm* — K&L Gates LLP

(57) ABSTRACT

The present invention relates generally to the field of nutrition, health and wellness. In particular the present invention relates to probiotics and ways to increase their effectiveness. One embodiment of the present invention relates to a combination of probiotics with SIgA and possible uses of this combination. For example a use of a composition comprising SIgA and at least one probiotic for the preparation of a product to treat or prevent inflammation is disclosed.

12 Claims, 7 Drawing Sheets

(56) References Cited

OTHER PUBLICATIONS

Yuvaraj, S., et al., "Human scFv SIgA expressed on Lactococcus lactis as a vector for the treatment of mucosal disease," Molecular Nutrition & Food Research, vol. 52, No. 8, Aug. 2008, pp. 913-920, XP009122203.
Diebel, L., et al., "Immunoglobulin a modulates inflammatory responses in an in vitro model of pneumonia," The Journal of Trauma, Nov. 2005, vol. 59, No. 5, pp. 1099-1106, XP009122209.
Amin, P., et al., "Secretory immunoglobulin a blunts gut-mediated priming of neutrophils in vitro," Journal of Trauma—Injury, Infection and Critical Care, vol. 64, No. 6 Jun. 2008, pp. 1437-1442, XP009122207.
Isolauri, E., et al., "Oral bacteriotherapy for viral gastroenteritis," Digestive Diseases and Sciences, vol. 39, No. 12, pp. 2595-2600.
Phalipon, A., et al., "Secretory Component: A New Role in Secretory IgA-Mediated Immune Exclusion in Vivo," Immunity, vol. 17, Jul. 2002, pp. 107-115.
Salminen, S., et al., "Probiotics: how should they be defined?" Trends in Food Science & Technology, vol. 10, 1999, pp. 107-110.
Corthesy, B., et al., "Roundtrip Ticket for Secretory IgA: Role in Mucosal Hemostasis," The Journal of Immunology, vol. 178, 2007, pp. 27-32.
International Search Report for International Application No. PCT/EP2009/057453 dated Sep. 14, 2009.
Written Opinion for International Application No. PCT/EP2009/057453 dated Sep. 14, 2009.
Advance Dairy Chemisty "Immunoglobulins in Mammary Secretions", pp. 426-427.
Medline Plus—Health Information from National Library of Medicine, pp. 1 and 2.

* cited by examiner

2x10⁷ LPR or BL818 combined with various amounts of SC/SIgA (μg)
Reminder: 1nM SC = 80 ng/ml; 1 nM SIgA = 400 ng/ml

Figure 5:

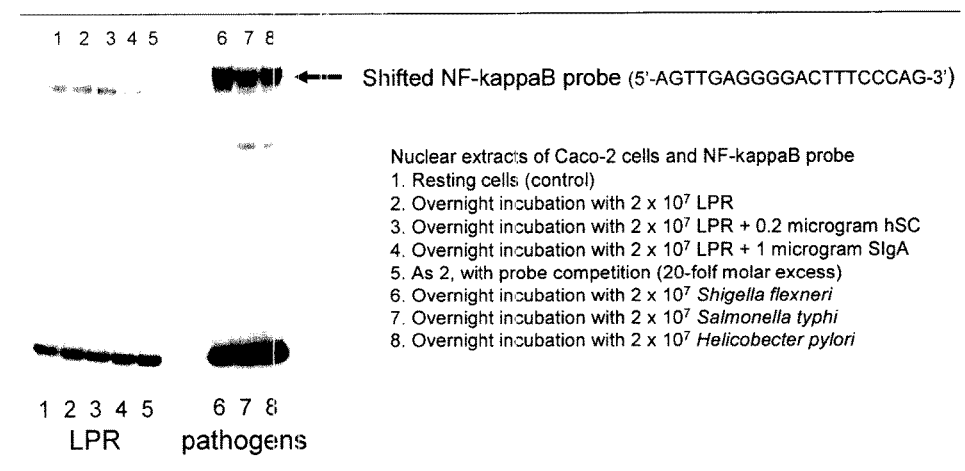

Shifted NF-kappaB probe (5'-AGTTGAGGGGACTTTCCCAG-3')

Nuclear extracts of Caco-2 cells and NF-kappaB probe
1. Resting cells (control)
2. Overnight incubation with $2 \times 10^7$ LPR
3. Overnight incubation with $2 \times 10^7$ LPR + 0.2 microgram hSC
4. Overnight incubation with $2 \times 10^7$ LPR + 1 microgram SIgA
5. As 2, with probe competition (20-folf molar excess)
6. Overnight incubation with $2 \times 10^7$ Shigella flexneri
7. Overnight incubation with $2 \times 10^7$ Salmonella typhi
8. Overnight incubation with $2 \times 10^7$ Helicobecter pylori 1 2 3 4 5       6 7 8
LPR           pathogens Western blot with anti-IkBalpha mAb

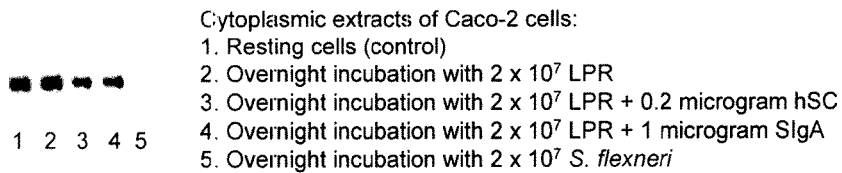

Cytoplasmic extracts of Caco-2 cells:
1. Resting cells (control)
2. Overnight incubation with $2 \times 10^7$ LPR
3. Overnight incubation with $2 \times 10^7$ LPR + 0.2 microgram hSC
4. Overnight incubation with $2 \times 10^7$ LPR + 1 microgram SIgA
5. Overnight incubation with $2 \times 10^7$ S. flexneri

PROBIOTICS, SECRETORY IGA AND INFLAMMATION

The present invention relates generally to the field of nutrition, health and wellness. In particular the present invention relates to probiotics and ways to increase their effectiveness. One embodiment of the present invention relates to a combination of probiotics with secretory IgA and possible uses of this combination.

Inflammation is the complex biological response of tissues to harmful stimuli, such as pathogens, damaged cells, or irritants. It is generally a protective attempt by the organism to remove the injurious stimuli as well as initiate the healing process for the tissue. However, non-appropriately regulated inflammation can lead to several diseases irrespective of the age of the subject.

Ageing is often associated with a dysregulation of the immune system, such as a noted decline in cell-mediated immune response concomitant with an increased humoral immune dysfunction (e.g. lower response to vaccine). Ageing is furthermore often associated with a status of low-grade inflammation. Consequently, in particular many elderly subjects are at increased risk of infectious and non-infectious diseases that contribute to morbidity and mortality.

Unwanted inflammation can be treated by proper medication. However, medication may always result in unwanted side effects and often requires the supervision of medical personnel. Consequently, there is a need in the art for compositions that can be administered—preferably on a day-to-day basis—without unwanted side effects and without the need to consult a doctor and that can be used to treat or prevent inflammation.

One way to achieve this object is to administer a food composition comprising probiotics.

Probiotic micro-organisms are known to have a beneficial effect on the health and well-being of the host. In the last few decades, the use of probiotic bacteria has gained considerable attention as a safe and accessible form of treatment for example for gastrointestinal diseases (Isolauri E, et al., Dig Dis Sci 1994, 39:2595-2600). Typical probiotic bacteria that have been employed in this respect belong to the *Lactobacillus* or the *Bifidobacterium* genus.

The effectiveness of probiotics depends, in part, on their ability to resist to digestive tract conditions and adhere to intestinal epithelium. Moreover, a critical aspect conditioning their potential benefit to the host is the probiotic cross-talk with the host's environment and their impact on epithelium barrier and its function.

While some probiotics already achieve very respectable result in terms of colonization of the gastrointestinal tract and interaction with the host, it would be desirable to have available a tool to further improve the effectiveness with which the probiotic micro-organisms colonize the gut and interact with the host.

It was consequently the object of the present invention to provide the art with a composition that has the same advantages as the administration of probiotics to a subject in need thereof but that is even more effective in treating or preventing inflammation than the administration of probiotics alone.

The present inventors have addressed this need and found that they could achieve this object by a use in accordance with claims 1 and a food composition in accordance with claim 12.

The present invention relates hence to a composition comprising secretory IgA and at least one probiotic and its use to treat, reduce or prevent inflammation.

Without wishing to be bound by theory, the inventors believe that SIgA and probiotics may form combinations that may potentiate the interaction of probiotics with the host and improve their health benefit.

The suggested mechanism of interaction of the immune combination with the intestinal mucosa of the host is presented in FIG. 1.

The first interaction of probiotics with the host occurs at the level of the gut mucosa. Among the key criteria for the selection of a probiotic micro-organism is its capacity to adhere to intestinal mucosa.

This adhesion seems to be required to block pathogen entry and contribute to modulate protective immune functions, for example.

One of the most characteristic features of the mucosal immune system in most mammals is the dominant presence of secretory antibodies, particularly secretory IgA (SIgA), an antibody class unique to mucosae.

Biosynthesis of polymeric IgA takes place in the mucosal lamina propria, and its transport across the epithelium lining the mucosal surfaces is ensured by the polymeric Ig receptor (pIgR) expressed by crypt and columnar epithelial cells.

In secretions, a significant portion of the pIgR termed the secretory component (SC) remains associated with polymeric IgA, releasing SIgA.

The release of SIgA into the lumen is dependent on the production of SC, whose expression is up-regulated after birth. pIgR appears to be critical to the stability and mucosal anchoring of the antibody (Phalipon et al. (2002) Secretory component: A new role in secretory IgA-mediated immune exclusion in vivo. Immunity 17:107-115).

Neonates, in which SIgA antibodies are barely detectable, depend on maternal IgG transferred through the placenta, and an exogenous supply of SIgA abundantly found in breast milk.

Together, this confers passive immunization in the gut essential to the protection of the host during the phase of shaping and maturation of the gastrointestinal immune system.

Hence the composition of the present invention will be in particular beneficial for newborns and infants (up to 2 years old), since they do not produce SIgA in sufficient amounts but rely on external supply.

The inventors presently believe that it is this association of SIgA with probiotics that potentiates the interaction of probiotics with the host, so that the health benefits for the host are improved.

The present inventors have identified that a combination of SIgA antibody with probiotics is capable of improving the interaction of the bacteria with a human cell line serving as a mimic of the gastrointestinal epithelium.

The present inventors have used in vitro Caco-2 epithelial cell monolayers to examine how SIgA favours the cross-talk between non-pathogenic bacteria and the epithelial surface. Two probiotic strains representative of the two main genders Lactobacilli and Bifidobacteria were evaluated as proof of principle, i.e. *Lactobacillus rhamnosus* NCC4007 (LPR) and *Bifidobacterium lactis* NCC2818 (BL818).

It was found that SIgA and/or SC, when associated with probiotics, promotes the interaction of probiotics with the host and modulates downstream processes involved in defense mechanisms.

This contributes to enhance the health benefits of probiotics. Through their combination with probiotics, SIgA and/or SC could optimally help trigger efficient protective host defense reactions, including immune responses, against various pathogens. Given their homeostatic effect (Corthesy B. (2007), J. Immunol.; 178:27-32), SIgA, combined with probiotics, will help to trigger an immune boosting effect while preventing any potential damaging inflammatory process.

Consequently, one embodiment of the present invention is a composition comprising SIgA and at least one probiotic for the preparation of a product to treat or prevent inflammation.

The present invention also relates to the use of a composition comprising SIgA and at least one probiotic for the preparation of a product to treat or prevent inflammation.

The present invention additionally relates to a composition comprising SIgA and at least one probiotic for use in the treatment and/or prevention of inflammation.

The treatment of inflammation includes the reduction of inflammation.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

All probiotic micro-organisms may be used in accordance with the present invention. Preferably, they are selected from the group consisting of *Bifidobacterium, Lactobacillus, Streptococcus* and *Saccharomyces* or mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (2818; CNCM I-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724), *Enterococcus faecium* SF 68 (NCIMB10415), and mixtures thereof.

The composition of the present invention may also contain prebiotics. The addition of prebiotics is beneficial as it can, when combined with probiotics, delivers synergistic effects in terms of the health benefits. A composition comprising a combination of prebiotics and probiotics is commonly known as a symbiotic composition.

"Prebiotic" means food substances that promote the growth of beneficial bacteria such as bifidobacteria or lactobacilli, and/or probiotics in the intestines. They are not broken down in the stomach or absorbed in the GI tract of the person ingesting them, but they are fermented by the gastrointestinal microflora and/or by probiotics.

The prebiotics that may be used in accordance with the present inventions are not particularly limited and include all food substances that promote the growth of probiotics in the intestine. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides, xylo-oligosaccharides, oligosaccharides of soy, glycosylsucrose (GS), lactosucrose (LS), lactulose (LA), palatinose-oligosaccharides (PAO), malto-oligosaccharides, pectins and/or hydrolysates thereof.

Typical inflammatory conditions that may be treated or prevented by the use of the present invention include but are not limited to acute inflammations such as sepsis, infections, burns and chronic inflammations such as inflammatory bowel disease, Crohn's disease, ulcerative colitis, necrotizing enterocolitis, skin inflammation, such as UV or chemical-induced skin inflammation, eczema, reactive skin, psoriasis, vitiligo, acne, liver inflammation, alcoholic cirrhosis, allergy, atopy, bone inflammation, rheumatoid arthritis, systemic lupus, Gougerot-Sjögren's syndrome, Reiter's syndrome, poliomyelitis, dermato-myositis, thyroiditis, Basedow, Hashimoto, type I diabetes, Addison's disease, auto-immunes hepatitis, celiac disease, Biermer's disease, multiple sclerosis, myasthenia, encephalomyelitis, eye inflammation, obesity-associated inflammation, age-related low-grade inflammation, Blau's syndrome, Alzheimer's disease, cardiovascular diseases, atherosclerosis, metabolic syndrome, gingivitis, paronditis and combinations thereof.

The composition of the present invention may also be used to control and/or alleviate an inflammatory reaction of the body.

The composition of the present invention can further be used to generate, improve or reinforce homeostasis and oral tolerance.

The product prepared by the use of the present invention may be a food product, an animal food product or a pharmaceutical composition. For example, the product may be a nutritional composition, a nutraceutical, a drink, a food additive or a medicament.

A food additive or a medicament may be in the form of tablets, capsules, pastilles or a liquid for example. Food additives or medicaments are preferably provided as sustained release formulations, allowing a constant supply of SIgA and probiotics for prolonged times.

The product is preferably selected from the group consisting of milk powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; tablets; and/or syrups.

Milk may be any milk obtainable from animal or plant sources and is preferably cows milk, human milk, sheep milk, goat milk, horse milk, camel milk, rice milk or soy milk.

Instead of milk, also milk derived protein fractions or colostrum may be used.

The composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. They may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. Further, they may contain an organic or inorganic carrier material suitable for oral or enteral administration as well as vitamins, minerals trace elements and other micronutrients in accordance with the recommendations of Government bodies such as the USRDA.

The composition of the present invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

If the composition includes a fat source, the fat source more preferably provides 5% to 40% of the energy of the formula; for example 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins, and mixtures thereof.

The product prepared by the present invention may be administered to humans or animals, in particular companion animals, pets or livestock. It has beneficial effects for any age group. Preferably, the product is intended in for infants, juveniles, adults or elderly. It may however also be administered to mothers during pregnancy and lactation to treat the infant.

The composition of the present invention will be effective as long as probiotics and SIgA are administered simultaneously, briefly one after the other, for example in a maximal timeframe of less than 60 minutes, preferably less than 30 minutes, more preferred less than 15 minutes and most preferred less than 5 minutes, and/or are combined prior to administration as already present in the food product.

However, it was found that the combination of probiotics and SIgA is in particular effective, if SIgA and probiotics are combined in complexes prior to administration. This has the advantage that the beneficial complexes do not need to form after consumption of the product, but that they are already present in the food product.

Consequently, one embodiment of the present invention relates to the use of a composition comprising SIgA and probiotics, wherein the SIgA and at least one probiotic are at least partially associated in the composition.

SIgA and at least one probiotic are preferably present as immune complexes, for example in a way that at least 90%, more preferably at least 95%, even more preferred all probiotic bacteria are present as immune complex in association with at least 1 SIgA molecule, for example with at least 5 SIgA molecules.

The composition may also contain at least one other kind of other food grade bacteria, preferably selected from the group consisting of lactic acid bacteria, bifidobacteria, enterococci or mixtures thereof. These other food grade bacteria may contribute to obtain a healthy gut microflora and will hence contribute to achieve the object of the present invention even more effectively.

The present invention also relates to a food composition comprising SIgA and at least one probiotic micro-organism. The SIgA and the probiotic micro-organism may preferably be combined in the food composition. SIgA and the probiotic micro-organism may be present in a stoichiometric ratio of at least 10:1, preferably at least 100:1, most preferably at least 2000:1 to 100000:1. Obviously, the more SIgA molecules are attached to the surface of the probiotic micro-organism the more effective this combination will be. The upper limit of SIgA saturation is determined by the surface of the probiotic micro-organisms and by the number of available binding sites for SIgA.

Typically, the probiotics will be effective in a large range amount. In general, it is preferred if the product comprises between $10^2$ and $10^{10}$ cells of probiotics per daily dose.

The amount of SIgA required to achieve an effect, is equally not limited. It is generally preferred if the product comprises between 0.0001 mg SIgA and 100 mg SIgA per daily dose.

Those skilled in the art will understand that they can freely combine all features of the present invention described herein, without departing from the scope of the invention as disclosed. In particular, features described for the uses of the present invention may be applied to the composition, e.g. the food composition, of the present invention and vice versa.

Further advantages and features of the present invention are apparent from the following Examples and Figures.

Figure 3:
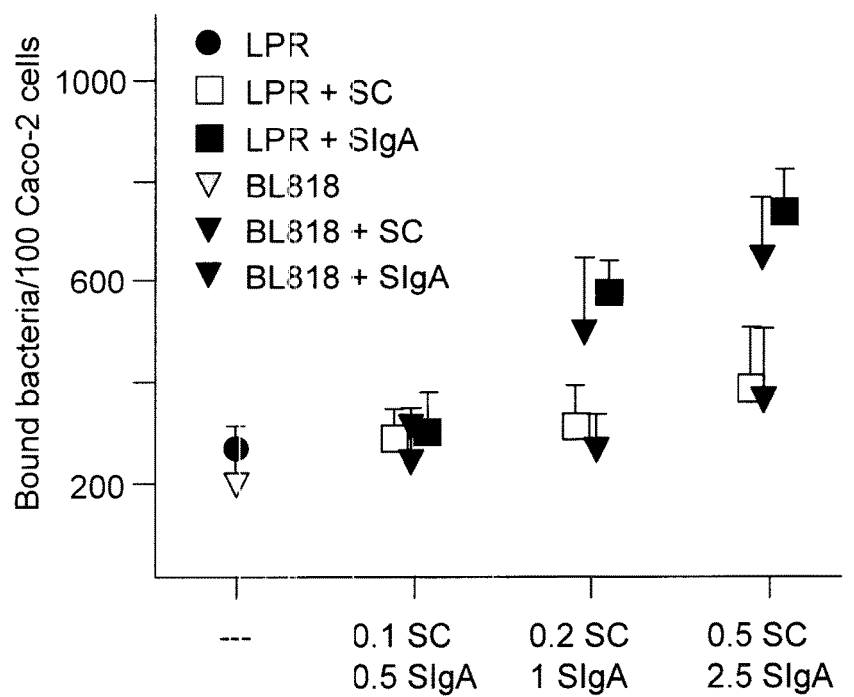

FIG. 3 shows the result of experiments testing the binding properties of two probiotic strains, *Lactobacillus rhamnosus* NCC4007 (LPR) and *Bifidobacterium lactis* NCC2818 (BL818), representative for the two main genders Lactobacilli and Bifidobacteria to epithelial cells and the influence of secretory IgA (SIgA) or secretory component (SC). Data are expressed as means CFU per 100 Caco-2 cells±SEM.

Figure 4:
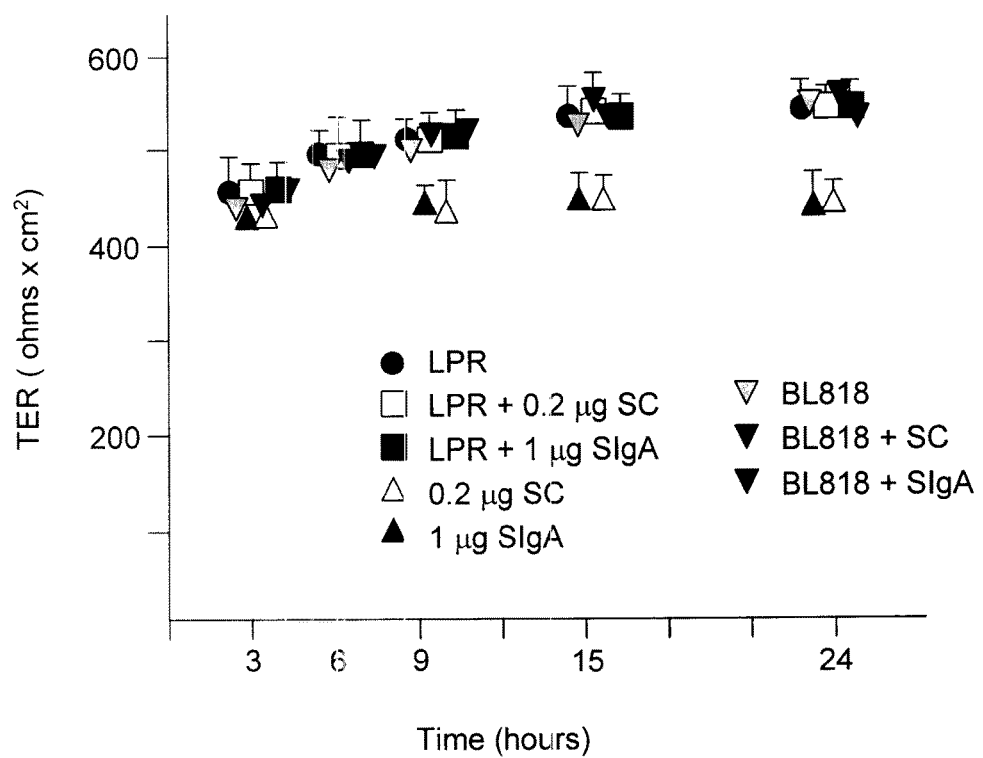

FIG. 4 shows the result of an experiment testing the effect of two probiotic strains, *Lactobacillus rhamnosus* NCC4007 (LPR) and *Bifidobacterium lactis* NCC2818 (BL818), representative for the two main genders Lactobacilli and Bifidobacteria, alone or in combination with SIgA or SC, on transepithelial electrical resistance (TER) measuring epithelial permeability. Data are expressed as means ohms per $cm^2$±SEM.

FIG. 5 shows the result of an experiment testing the effect of LPR, combined or not with SIgA or SC, on NF-κB activation in Caco-2 cell monolayer. Decrease in NF-kB binding activity is indicative of attenuated inflammatory pathway(s) within the Caco-2 cell.

Figure 6:
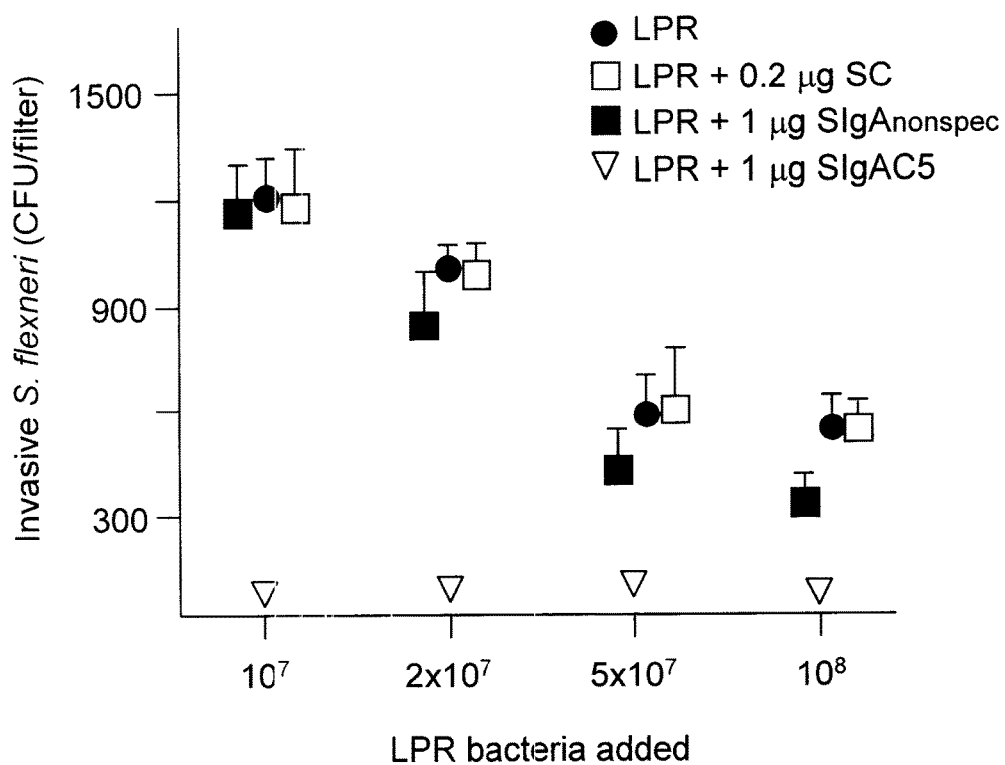

FIG. 6 shows the result of an experiment testing the effect of LPR, combined or not with SIgA or SC, on *S. flexneri* invasion of Caco-2 cell. Two monoclonal SIgA molecules were used: a non-specific SIgA (SIgAnon-specific) recognizing a *Salmonella* epitope, and a specific anti-*S. flexneri* SIgA (SIgAC5). Data are expressed as means CFU per transwell filter±SEM.

Figure 7:
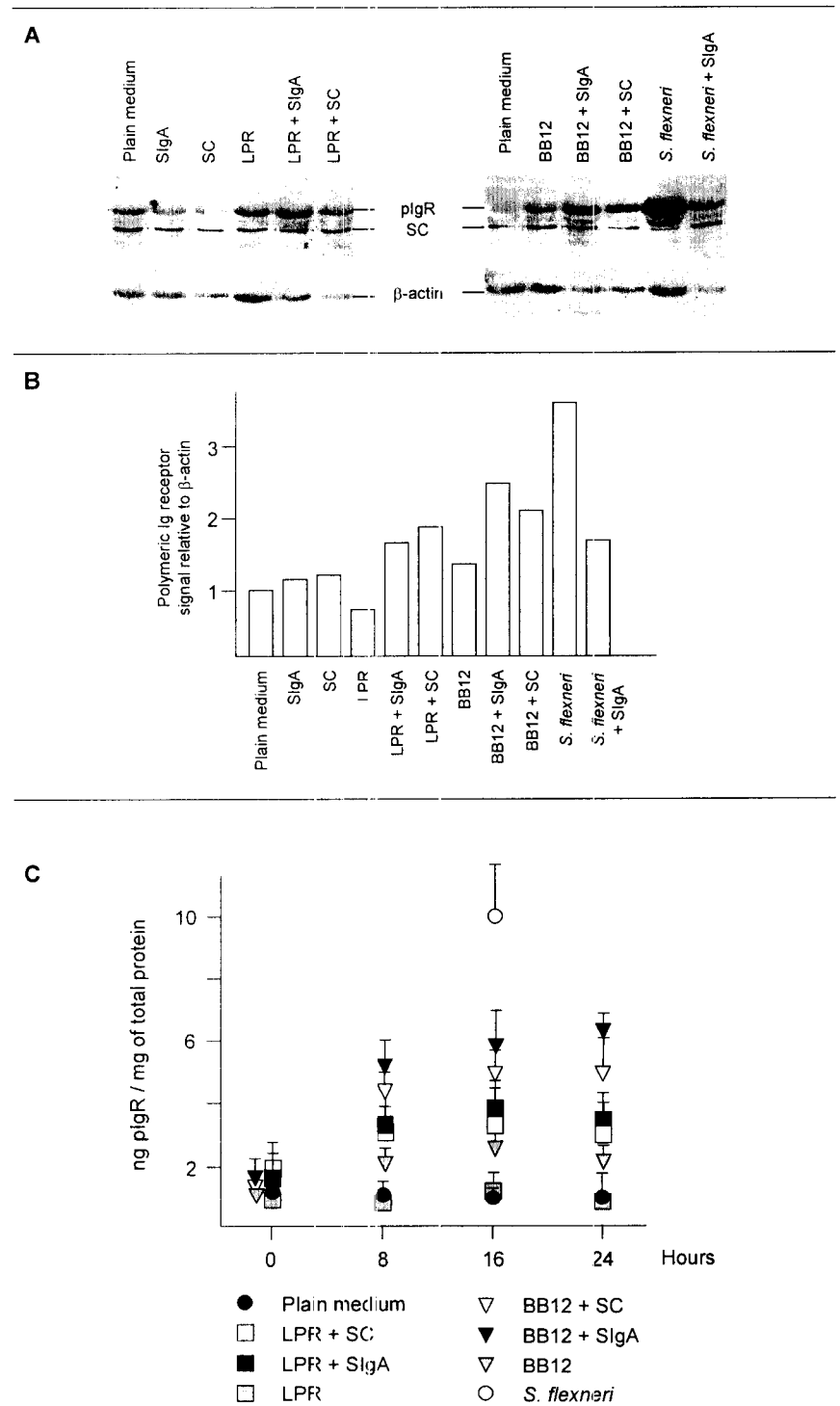

FIG. 7 shows the result of an experiment testing the effect of probiotics on polymeric Ig receptor (pIgR) expression in a Caco-2 monolayer. (A) Different treatments were tested at 16 h, including combination of probiotics with non-specific SIgA and combination of *S. flexneri* with specific anti-*S. flexneri* SIgA (western blot). (B) Semi-quantitative analysis of pIgR expression levels normalized to β-actin by densitometric analysis of the bands identified in the gels in A. (C)

Kinetic of pIgR expression over 24 h incubation of Caco-2 cells with various preparations (ELISA).

EXAMPLE 1

Binding to Epithelial Cells

Approximately $10^6$ Caco-2 cells were seeded per 1 cm² Transwell filter. Cells were incubated for 16 h at 37° C. with different doses of bacteria, indicated in the figure legend in absence of antibiotic or FCS. Fresh overnight cultures of LPR, BL818 and *E. coli* TG-1 bacteria were used. Cells were then washed prior to enumeration. Bound bacteria were counted by plating on MRS or LB plates. For each experiment, triplicate tests were performed. Data were expressed as means of bound bacteria per 100 Caco-2 cells±SEM. Triplicates were performed for each experiment. In a subsequent experiment, cells were incubated with $2 \times 10^7$ bacteria for 16 hours at 37° C., in the presence of increasing doses of either SIgA or SC as indicated in the legend to FIG. 3. Cells were then washed prior to enumeration. Bound bacteria were counted by plating on MRS or LB plates. For each experiment, triplicate tests were performed. Data were expressed as means of bound bacteria per 100 Caco-2 cells±SEM. Triplicates were performed for each experiment.

Figure 1:
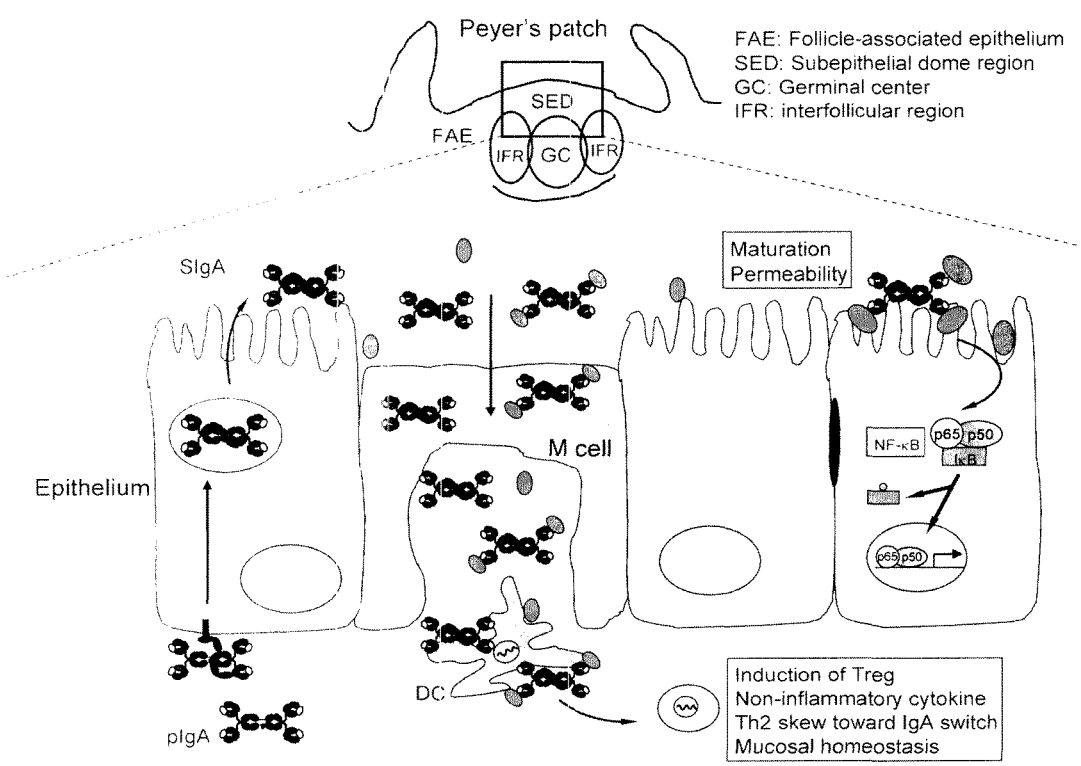
FIG. 1 shows schematically how SIgA is believed to improve the effects of commensal bacteria, when associated with them by increasing the interaction with the intestinal mucosa of the host. Depicted are possible and documented routes of interaction of SIgA associated with commensal bacteria with the host intestinal mucosa.
Figure 2:
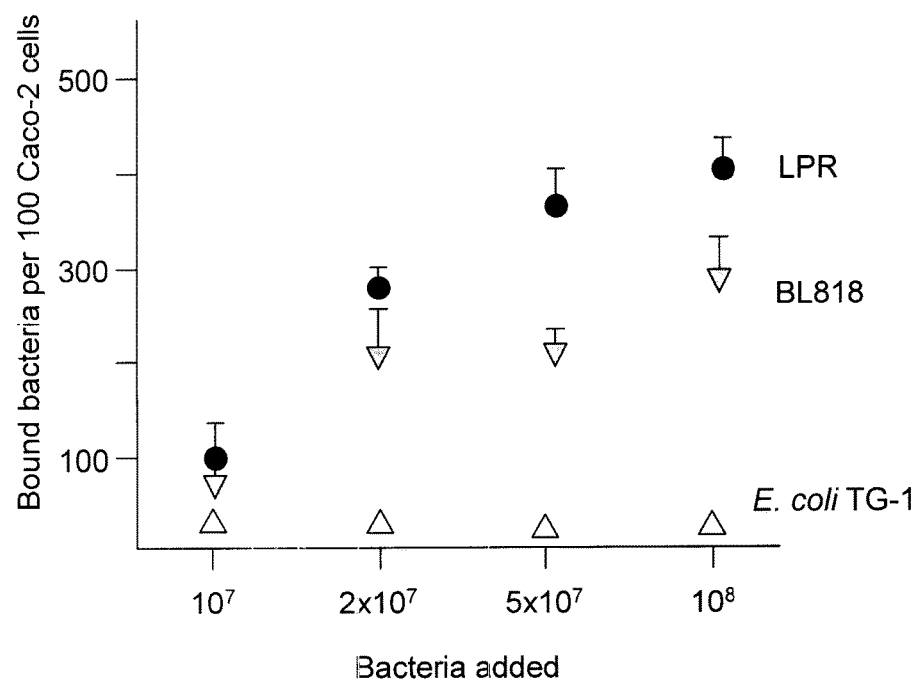
FIG. 2 shows the result of experiments testing the binding properties of two probiotic strains, *Lactobacillus rhamnosus* NCC4007 (LPR) and *Bifidobacterium lactis* NCC2818 (BL818), representative for the two main genders Lactobacilli and Bifidobacteria to epithelial cells. Data are expressed as means CFU per 100 Caco-2 cells±SEM.

A preferential binding to polarized Caco-2 cells of LPR and BL818 is observed in comparison to *E. coli* TG-1 (FIG. 2). There is a dose-dependent binding capacity of probiotics to intestinal epithelial cells. It can be observed that binding properties could be differentiated between the two strains.

For subsequent experiments $2 \times 10^7$ CFU of probiotics were used, as this amount did not lead to any pH change in the medium on one hand, and showed an efficient binding ratio on the other hand.

Increasing the dose of monoclonal SIgA potentiated the capacity of both LPR and BL818 to bind to polarized Caco-2 cell monolayers. Secretory component by itself did not exhibit such properties (FIG. 3). The 1 µg dose of SIgA that confers a significant improvement in probiotic binding capacity was selected for subsequent experiments. This dose enables a final complex constituted of 50,000 to 100,000 units of SIgA for 1 bacterium.

Results are shown in FIGS. 2 and 3.

EXAMPLE 2

Barrier Function in Polarized Caco-2 Cell Monolayer

Approximately $10^6$ Caco-2 cells were seeded per 1 cm² Transwell filter. Cells were incubated for 24 h at 37° C. with $2 \times 10^7$ CFU of bacteria in absence of antibiotic or FCS. Bacteria were tested either alone or in combination with SIgA or SC at concentrations indicated in the legend to FIG. 4. Transepithelial electrical resistance (TER) was measured at 3, 6, 9, 15 and 24 h. Controls include incubation with SIgA and SC alone. Triplicates were performed for each experiment.

A 20-25% increase in transepithelial electrical resistance (TER) resulted from the incubation of polarized Caco-2 cell monolayer with LPR or BL818 alone, suggesting that probiotics potentiated epithelial barrier function. This remained true when the bacteria were combined with SIgA or SC (FIG. 4). SIgA or SC by themselves did not lead to any TER change.

Results are shown in FIG. 4.

EXAMPLE 3

NF-κB Activation in Polarized Caco-2 Cell Monolayer

Approximately $10^6$ Caco-2 cells were seeded per 1 cm2 Transwell filter. Cells were incubated for 16 h at 37° C. with $2 \times 10^7$ CFU of LPR in absence of antibiotic or FCS. Bacteria were tested either alone or in combination with SIgA or SC at concentrations indicated in the legend to FIG. 5. *S. flexneri, S. typhi* and *H. pylori* ($2 \times 10^7$ CFU) were used as pathogenic controls. Nuclear and cytoplasmic extracts were prepared and analysed by electrophoretic mobility shift assay (EMSA) and Western blot using anti-IκBα-specific monoclonal antibody. Triplicates were performed for each experiment.

Exposure to pathogenic bacteria led to much more pronounced activation of nuclear NF-κB compared to non-pathogenic bacteria (FIG. 5).

Disappearance of IκBα (lower panel) reflects activation of the pathway leading to nuclear translocation of NF-κB. In that respect, while LPR alone has a mild effect on NF-κB activation, combination of LPR with SIgA or SC reduced NF-κB activation in Caco-2 cells (BL818 not tested). Incubation of epithelial cells with pathogenic *S. flexneri* led to total disappearance of IκBα expression.

Results are shown in FIG. 5.

EXAMPLE 4

Anti-Pathogenic Activity

Approximately $10^6$ Caco-2 cells were seeded per 1 cm² Transwell filter. Cells were incubated for 16 h at 37° C. with $2 \times 10^7$ CFU of LPR in absence of antibiotic or FCS. LPR was tested alone or in combination with either 0.2 µg of SC, 1 µg of polyclonal SIgA or 1 µg of specific anti-*S. flexneri* LPS SIgAC5. After incubation with LPR cells were washed and then incubated with $10^7$ *S. flexneri* for 6 hours, washed again and incubated with 50 mg/ml gentamycin for 45 min. Finally, cells were lysed and intracellular *S. flexneri* were enumerated on LB agar plates. Triplicates were performed for each experiment.

Addition of LPR reduced infection of polarized Caco-2 cell monolayer by *S. flexneri* in a dose dependent manner. The effect was highly enhanced upon combination with SIgA. Full prevention of infection was achieved when *S. flexneri* LPS-specific SIgAC5 antibody was used (FIG. 6).

Results are shown in FIG. 6.

EXAMPLE 5

Expression of Polymeric IG Receptor in Polarized Caco-2 Cell Monolayer

Approximately $10^6$ Caco-2 cells were seeded per 1 cm² Transwell filter. Cells were incubated for 16 h at 37° C. with $2 \times 10^7$ CFU of LPR or BL818 in absence of antibiotic or FCS. Probiotics were tested alone or in combination with either 0.2 µg of SC, 1 µg of polyclonal SIgA. Control *S. flexneri* was tested alone or in combination with 1 µg of specific anti-*S. flexneri* LPS SIgAC5. After washing, Caco-2 cells were directly recovered from the Transwell filters and lysed. Nuclei were removed and cell debris as well as cytoplasms were analysed by Western blot using anti-pIgR antibody and antisera to human SC and β-actin as controls. Triplicates were performed for each experiment.

In a subsequent experiment cells were incubated following the same procedure and then recovered from the transwell filter at 8, 16 and 24 h of incubation. Quantitative analysis of pIgR was performed by ELISA on cell debris/ cytoplasm fractions. Total proteins were determined by BCA protein assay. Values were normalized to protein content and data expressed as means of ng pIgR/mg of total protein±SEM.

pIgR expression in epithelial cells was normalized to β-actin expression. As revealed by Western blot (upper panel) and densitometric analysis of the respective bands (lower panel) there was an increase of pIgR level following overnight exposure of polarized Caco-2 monolayers to combinations of LPR or BL818 with either SIgA or SC compared to probiotics alone (FIG. 7a). Specific anti-*S. flexneri* LPS SIgAC5 prevented interaction of the pathogen with the Caco-2 cell polarized monolayer, thus explaining the decrease in pIgR expression when compared to *S. flexneri* treatment alone.

The results further showed a time-dependent increase of polymeric Ig receptor (pIgR) level following exposure of polarized Caco-2 cell monolayers to probiotic combinations with SIgA or SC (FIG. 7b).

Results are shown in FIG. 7.

The invention claimed is:

1. A method for treating inflammation, the method comprising:
administering a therapeutically-effective amount of a composition comprising an isolated secretory IgA (SIgA) of 0.0001 mg to 10 mg per daily dose and at least one probiotic of $10^2$ to $10^{10}$ cells per daily dose, wherein the SIgA and the at least one probiotic are associated by a chemical bond as complexes in the composition, to a subject having the inflammation.

2. The method of claim 1 wherein the composition generates, improves or reinforces homeostasis and oral tolerance.

3. The method of claim 1 wherein the at least one probiotic is selected from the group consisting of *Bifidobacterium, Lactobacillus, Streptococcus, Saccharomyces* and mixtures thereof.

4. The method of claim 1, wherein the composition is selected from the group consisting of a food product, an animal food product and a pharmaceutical composition.

5. The method of claim 1, wherein the subject is a human.

6. The method of claim 1, wherein the composition controls and/or alleviates inflammatory reaction.

7. The method of claim 1, wherein the composition comprises at least one other kind of other food grade bacteria.

8. The method of claim 1, wherein the composition further contains at least one prebiotic.

9. The method of claim 1 wherein the at least one probiotic is selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii, Lactobacillus reuteri* and mixtures thereof.

10. The method of claim 1, wherein the composition comprises at least one other kind of other food grade bacteria selected from the group consisting of lactic acid bacteria, bifidobacteria, enterococci and mixtures thereof.

11. The method of claim 1, wherein the at least one probiotic is selected from the group consisting of *Lactobacillus rhamnosus* NCC4007 (LPR) and *Bifidobacterium lactis* NCC2818 (BL818).

12. The method of claim 1, wherein the SIgA and the at least one probiotic micro-organism are present in a stoichiometric ratio of at least 10:1.

* * * * *